United States Patent [19]

Stabley, Jr.

[11] 4,365,054

[45] Dec. 21, 1982

[54] ETHYLENE GLYCOL TEREPHTHALATE PRODUCTION

[75] Inventor: Bernard D. Stabley, Jr., Chester, Va.

[73] Assignee: The Firestone Tire & Rubber Company, Akron, Ohio

[21] Appl. No.: 603,479

[22] Filed: Aug. 11, 1975

[51] Int. Cl.$^3$ ............... C08G 63/04; C08G 63/14; C08G 63/34

[52] U.S. Cl. ............... 528/277; 528/279; 528/280; 560/94; 560/95; 560/201

[58] Field of Search ............ 260/475 P; 528/277, 528/279, 280; 560/94, 95, 201

[56] References Cited

U.S. PATENT DOCUMENTS

| | | | |
|---|---|---|---|
| 3,056,817 | 10/1962 | Werber et al. | 260/475 P |
| 3,056,818 | 10/1962 | Werber | 260/475 P |
| 3,245,959 | 4/1966 | Roeser | 260/475 P |
| 3,326,965 | 6/1967 | Schulthesis et al. | 260/475 P |
| 3,870,688 | 3/1975 | Makimura et al. | 260/75 R |
| 3,965,071 | 6/1976 | McClelland | 260/75 R |

FOREIGN PATENT DOCUMENTS

| | | |
|---|---|---|
| 2434213 | 2/1975 | Fed. Rep. of Germany . |
| 1027266 | 4/1966 | United Kingdom . |

OTHER PUBLICATIONS

McClelland, as cited in Chem. Abstracts, 83, 194081j (1975).

*Primary Examiner*—Harold D. Anderson
*Assistant Examiner*—Nathan M. Nutter

[57] ABSTRACT

A glycol and terephthalic and other aromatic acids are esterified using alkali metal titanates as catalysts and the catalysts are used in polymerization of the ester.

9 Claims, No Drawings

ETHYLENE GLYCOL TEREPHTHALATE PRODUCTION

PRIOR ART

The organic and halogen compounds of titanium and their hydrolysis products (i.e., $TiO_2$) have been used as catalysts in transesterification processes of producing polyesters. They have also been used as catalysts for producing cross-linked polyesters for paints, etc. See, for example, Swiss Pat. No. 455,290 (69 Chem.Abst. 67924x); Austrian Pat. No. 259,232 (68 Chem.Abst. 50570k); Japanese Pat. No. 1932 of 1968 (68 Chem.Abst. 105642t); German Pat. No. 1,237,316 (68 Chem.Abst. 3383s) and Japanese Pat. No. 18748 of 1960 (55 Chem.Abst. 21673h).

Titanic acid has been used as a polymerization catalyst. See Japanese Pat. No. 18748 of 1960 (see 55 Chemical Abstracts 1961).

Ammonium and amine titanates are described as general purpose esterification catalysts in German Pat. Nos. 1,173,473 and 1,103,335, and $(NH_4)_4TiO_4$ is disclosed in Japanese No. 4,599 as a polyesterification catalyst. Various quaternary amine salts are disclosed for this purpose in Caldwell U.S. Pat. No. 2,727,881.

British Pat. No. 892,743, in line 81 of page 1, lists sodium titanate as a catalyst for esterification. However, Table I and the footnote on page 2 refer to it as having been prepared by reacting one mol of tetrabutyl titanate with two mols of NaOH, and this would yield the compound $Na_2Ti(OR)_2$ or a mixture containing a high percentage of this compound.

SUMMARY OF THE INVENTION

The titanates of the alkali metal elements (lithium, sodium, potassium, rubidium and caesium) catalyze the esterification of ethylene glycol and butane diol and other glycols having the formula HO—R—OH in which R can be $(CH_2)_n$ in which n equals 2 to 4 or 8 or more in a linear or branched-chain or a cyclo-containing hydrocarbon, including compounds of the formula

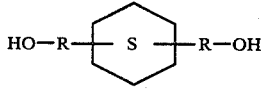

in which each R equals $(CH_2)_n$ in which n is zero or 1 or even 2 to 4 or more. Examples, in addition to the preferred ethylene glycol and butane diol include propylene glycols, ethylhexyl glycol cyclohexyl glycols, dimethylol cyclohexane, etc. Preferably terephthalic acid is used although acids which may be used include acids of the formula HOOC—R—COOH in which R is a phenyl, naphthyl or other hydrocarbon ring substituted in any position in the ring by sulfonic acids or their salts, halogens, etc. such as 5-sulfoisophthalic acid or its sodium salt, tetrachloroterephthalic acid, isophthalic acid, 2,6-naphthoic acid and 2,7-naphthoic acid, etc., and polymerization of the esters. It is found that these catalysts produce a high percentage of the ester with a minimum amount of by-products of a harmful nature, such as ethers; and they reduce the time required for polymerization.

CATALYST PREPARATION

The catalysts were prepared as follows:

The carbonates of the various metals were fused with titanium dioxide according to the following equation in order to obtain titanates that were free of organic matter:

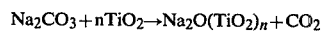

The potassium and sodium titanates that were used were said by the manufacturer to be 95 percent pure $K_2O(TiO_2)_4$ and $Na_2O(TiO_2)_4$, respectively. The lithium, caesium and rubidium titanates of the formula $M_2O(TiO_2)_n$ can be used in which the molar ratio of $TiO_2/M_2O$ varies from 0.05/1 up to, for example, as much as 2 to 10 or 20 up to 25 or more. The catalytic activity decreases as the amount of titanium decreases, being most active when the molar ratio of $TiO_2/M_2O$ is between 3/1 and 5/1.

PRODUCTION OF ESTER

In producing the ester, 1.2 to 2.0 mols of ethylene or other glycol, and preferably substantially 1.4 to 1.8 mols are used per 1 mol of terephthalic or other acid. In the laboratory, no water is used although in commercial operations the situation may be different. The reaction is carried out under pressure at a temperature substantially 25° to 75° C. above the boiling point of the glycol. The reaction conditions are, for example, substantially 225° C. to 250° C. for an ethylene glycol reaction, at 10 to 40 psig. with a reaction time of substantially 2 to 10 hours or thereabouts.

Three thousand grams of prepared paste were heated at the preferred temperature of 225° C. and pressure of 20 psig. using different alkali metal titanates as catalysts, in amounts ranging from substantially 0.005 to 0.030 percent or more by weight of catalyst. The headings A, B, C, D, E and F in the following table stand, respectively, for commercially available lithium, sodium, potassium, rubidium, caesium and potassium titanates of the approximate formula $M_2O(TiO_2)_4$. Heading G is included to refer to the use of tetramethyl ammonium acetate in combination with potassium titanate. The control contained 0.0175 percent lithium as lithium acetate, based on the weight of the ethylene glycol. The reacting mixtures were sampled after 4 hours and again after 7 hours with the following results:

TABLE I

| CATALYST | A | B | C | D | E | F | G | CONTROL | NO CATALYST |
|---|---|---|---|---|---|---|---|---|---|
| % Ti in charge | 0.029 | 0.029 | 0.029 | 0.020 | 0.019 | 0.0073 | 0.0073 | | |
| 4 hr. residence: | | | | | | | | | |
| COOH, µeq/gm | 471. | 597. | 473. | 400. | 429. | 892. | 584. | 742 | 3832 |
| Ethers, % | 0.62 | 0.77 | 0.60 | 0.58 | 0.44 | 1.23 | 0.67 | 0.84 | 2.95 |
| EG, % | 4.4 | 6.0 | 5.3 | 4.8 | 4.2 | 6.6 | 6.1 | 15.2 | 5.9 |
| DEG, % | 0.09 | 0.13 | 0.09 | 0.06 | 0.05 | 0.25 | 0.14 | 0.54 | 0.96 |
| MHET, % | 5.8 | 6.0 | 4.6 | 4.9 | 5.5 | 7.4 | 6.8 | 8.9 | 4.0 |
| BHET, % | 18.8 | 24.5 | 24.0 | 22.8 | 19.1 | 21.5 | 25.4 | 24.6 | 13.2 |
| TEREPHTHALIC ACID, % | 0.2 | 1.6 | 0.2 | 0.2 | 0.35 | 9.5 | 1.6 | 2.2 | 20.3 |

TABLE I-continued

| CATALYST | A | B | C | D | E | F | G | CONTROL | NO CATALYST |
|---|---|---|---|---|---|---|---|---|---|
| 7 hr. residence: | | | | | | | | | |
| COOH, μeq/gm | 270. | 354. | 383. | 389. | 432. | 416. | 404. | 584. | 330. |
| Ethers, % | 0.73 | 1.09 | 0.73 | 0.64 | 0.59 | 1.43 | 0.96 | 0.96 | 3.15 |
| EG, % | 4.1 | 5.1 | 5.4 | 5.6 | 4.7 | 5.8 | 6.0 | 4.4 | 4.7 |
| DEG, % | 0.11 | 0.13 | 0.10 | 0.10 | 0.006 | 0.22 | 0.14 | 0.29 | 0.73 |
| MHET, % | 5.5 | 4.5 | 4.8 | 5.1 | 5.5 | 4.8 | 5.7 | 5.6 | 3.7 |
| BHET, % | 17.6 | 23.8 | 24.7 | 22.7 | 19.9 | 17.2 | 25.1 | 18.7 | 17.6 |
| TEREPHTHALIC ACID, % | 0.4 | 0.2 | 0.3 | 0.2 | 0.26 | 0.3 | 0.3 | | 0.4 |

EG = Ethylene Glycol
DEG = Diethylene Glycol
MHET = Mono(hydroxyethyl)terephthalate
BHET = Bis(hydroxyethyl)terephthalate In the table the recorded amounts of COOH are the titratable carboxyl groups found regardless of the form of the compounds in which they occur, whether as metal carboxylates, oligomers, etc. The other analyses were made by gas chromatography. The amount of terephthalic acid is free terephthalic—i.e., not esterfied and is included in titrated carboxyl recorded as COOH, as is also the MHET which has the formula

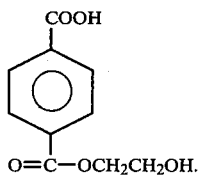

The BHET does not contain terminal carboxyl but has the formula

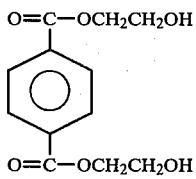

The monomers esterified using titanate catalysts, are esterified as well in four hours as the control is in 7 hours, or more completely, as shown in the examples by the COOH values of 584 in the control after 7 hours compared with the values 471, etc. after 4 hours. The table shows that without catalyst the ether yield is appreciably higher than with a catalyst. The catalyst used under F is low, much lower than under the other potassium catalyst C, so the reduction of ethers is not so pronounced, but is significantly better than when no catalyst was used.

The EG figures, show that after 7 hours, more was used up than after 4 hours.

The DEG figures represent free diethylene glycol whereas the ethers represent total diethylene (or triethylene) glycol including both free and esterified. The figures representing esterification with metal titanates are much lower than when no catalyst was used, and are all better than the control (with lithium acetate).

The addition of 0.03 percent tetramethylammonium acetate (TMAA) (based on the weight of glycol) to the reaction mixture containing K₂TiO₃, as shown in column G, reduced the ether-retarding effect when a small amount (0.0073%) of the titanate was used, as compared to column F. When a larger amount of titanate (0.029%) was used TMAA reduced the rate of esterification as well as the rate of ether formation.

POLYMERIZATION OF ESTER

There are two general procedures.

(A) Adding titanate to terephthalic acid-ethylene glycol paste

A series of polymerization reactions were run, using different titanates.

Two thousand grams of esterified monomer was charged to a polymerization vessel equipped with a stirrer to the shaft of which was attached a torque meter for measuring the viscosity of the polymerization reaction mixture as the reaction progressed. The catalyst was charged to the vessel at the same time as the monomer. The vessel was evacuated several times and flushed with nitrogen to remove the air. The vessel was heated to melt the monomer and then evacuated, the vacuum being maintained as indicated below.

Temperature: 245° C. vacuum applied.
Temperature to 270° C. pressure to 27.7 Hg vacuum over a period of 78 minutes.
Temperature to 280° C. pressure to 10 mm. Hg vacuum over a period of 66 minutes.
Temperature to 285° C. pressure to about 0.1 mm. Hg vacuum to complete polymerization.

Thus, a temperature in the range of 230° to 300° C. or thereabout is satisfactory. Polymerization was considered complete when the melt viscosity, measured by the torque meter, reached a maximum and became constant, normally about 80 to 95 pound-inches. The vacuum was released by bleeding nitrogen into the vessel which prevented oxidation. On completion of the polymerization it was found advantageous with the equipment used to pressure the reaction mixture from the vessel through a valve at the top which was opened, and the polymer was extruded slowly through a valve at the bottom of the reactor and the polymer was quenched in ice water. The concentration of titanate catalyst in the melt was 0.02 to 0.03 percent as titanium based on the 2000 grams of monomer.

The results are recorded in the following table. The viscosity is reported as intrinisic viscosity in units of deci-liters/gram. The time of polymerization in the examples is the time required to produce a torque of 90 pound-inches, except that the control never reached this torque. The carboxyl end groups present are reported as $\mu$ eq/gm, and the ether as weight percent. Ethers increase during polymerization, carboxyl end groups decrease.

Antimony trioxide, a usual catalyst, was added to certain runs to compare the effectiveness of the titanates of the invention, and it was found that the titanates are as efficient as the antimony trioxide.

TABLE II

| CATALYST | I.V. dl/gm | COOH Ends μeq/gm | ETHER Wt. % | POLYM. TIME HRS. |
|---|---|---|---|---|
| $Li_2TiO_3$ | 0.64 | 32.5 | 1.33 | 6.0 |
| $Na_2TiO_3$ | 0.74 | 24.5 | 2.15 | 5.0 |
| $K_2TiO_3$ | 0.93 | 22.3 | 1.62 | 4.0 |
| $RB_2TiO_3$ | 0.77 | 39.8 | 2.22 | 3.75 |
| $Cs_2TiO_3$ | 0.76 | 33.4 | 2.11 | 3.25 |
| Control* | 0.69 | 29.0 | 2.11 | 6.25 |

*Polymerization catalyst was antimony trioxide.

The rubidium and caesium titanates gave the shortest polymerization times but are too costly for commercial operations. The potassium titanate is preferred.

(B) Adding additional titanate to esterified monomer

In another series of experiments, monomer produced as described was polymerized using additional potassium titanate and/or antimony trioxide as polymerization catalyst.

When additional titanate is added before polymerization, the polymerization time is shortened (see ADDITIONAL TITANATE ADDED). With additional titanate, e.g. 0.034 percent as titanium, in Table III, the amount of antimony trioxide added makes no significant change in polymerization time, as shown in Table III. The "EST. TIME" is the time required to esterify the monomer as indicated in Table I.

TABLE III

| ESTERIFICATION CATALYST* | CONC. % Ti | EST. TIME, HRS. | ADDITIONAL TITANATE ADDED | $Sb_2O_3$** | I.V. dl/gm | POLYM. TIME |
|---|---|---|---|---|---|---|
| Potassium Titanate | .0073 | 7 | No | Normal | 0.74 | 4.50 hours |
| Potassium Titanate | .029 | 3 | No | Normal | 0.76 | 3.50 hours |
| Potassium Titanate-TMAA | .029 | 3 | No | Normal | 0.73 | 3.75 hours |
| Potassium Titanate-TMAA | .0073 | 7 | No | ½ | 0.71 | 5.25 hours |
| Potassium Titanate-TMAA | .029 | 7 | No | ½ | 0.74 | 4.75 hours |
| TMAA | — | 7 | Yes** | ½ | 0.81 | 3.75 hours |
| Potassium Titanate | .029 | 3 | Yes | ½ | 0.76 | 3.50 hours |
| Potassium Tetanate | .029 | 3 | Yes | None | 0.74 | 3.75 hours |

*Potassium Titanate is the commercially available product, TMAA is tetramethylammonium acetate.
**Normal concentration of $Sb_2O_3$ is 450 ppm as Sb. ½ concentration of $Sb_2O_3$ is 225 ppm as Sb.
***.034 percent as titanium.

The table makes it clear that the runs in which added titanate was included are most economical in reaction time. Not only are the polymerization times reduced but they are accomplished with esters obtained in esterification time of three hours rather than in seven hours.

I claim:

1. The method of producing an ester of ethylene glycol and terephthalic acid which comprises catalyzing the esterification of 1.2 to 2 mols of ethylene glycol with 1 mol of terephthalic acid under conditions ranging between 225° to 250° C. and a pressure of 10 to 40 psig, using as a catalyst 0.005 to 0.030 part of $M_2O(TiO_2)_n$ per hundred parts of the reactants, in which M is from the class consisting of lithium, potassium, sodium, rubidium and caesium, and n is 0.05 to 25.

2. The method of claim 1 in which the ratio of $TiO_2/M_2O$ is not greater than 10.

3. A process for the preparation of a linear high molecular weight film and fiber-forming polyester which comprises esterifying terephthalic acid with ethylene glycol under direct esterification conditions in the presence of at least a catalyzing amount of a titanium compound selected from the group consisting of sodium titanate and lithium titanate, the molecular ratio of terephthalic acid to glycol in said esterification being between 1.0:1.2 to 1.0:2, the temperature range being about 225° C. to about 250° C.; and then polymerizing the product of said esterification in the presence of said titanium compound as the only catalyst for said polymerization to form said linear high molecular weight film and fiber-forming polyester.

4. The method of producing an ester of ethylene glycol and terephthalic acid which comprises catalyzing the esterification of 1.2 to 2 mols of ethylene glycol with 1 mol of terephthalic acid under temperature conditions ranging between 225° to 250° C., using a catalytic amount of $M_2O(TiO_2)_n$, in which M is selected from the group consisting of sodium and lithium and n is 0.05 to 25.

5. A process for the preparation of a linear high molecular weight film and fiber-forming polyester which comprises esterifying terephthalic acid with ethylene glycol under direct esterification conditions in the presence of at least a catalyzing amount of a compound of the formula $M_2O(TiO_2)_n$, in which M is from the class consisting of lithium, potassium, sodium rubidium and caesium and n is 0.05 to 25, the molecular ratio of terephthalic acid to glycol in said esterification being between 1.0:1.2 and 1.0:2, the temperature range being about 225° C. to about 250° C.; and then polymerizing the product of said esterification in the presence of said titanium compound as a catalyst for said polymerization to form said linear high molecular weight film and fiber-forming polyester.

6. The process of claim 5 wherein the titanate catalyst is potassium titanate.

7. The process of claim 5 wherein additional catalyst comprising at least one catalyst from the group selected from the titanate compounds named in claim 5 and antimony trioxide is added to the product of esterification prior to polymerization.

8. The process of claim 5 wherein additional titanate catalyst from the group named in claim 5 is added to the product of esterification prior to polymerization.

9. The process of claim 8 wherein the additional titanate catalyst is potassium titanate.

* * * * *